US 6,652,553 B2

(12) United States Patent
Davison et al.

(10) Patent No.: US 6,652,553 B2
(45) Date of Patent: Nov. 25, 2003

(54) SURGICAL TOOL FOR USE IN EXPANDING A CANNULA

(75) Inventors: Thomas W. Davison, North Attleboro, MA (US); Adam Sher, North Attleboro, MA (US); John D. Unger, Wrentham, MA (US)

(73) Assignee: Endius Incorporated, Plainville, MA (US)

( * ) Notice: Subject to any disclaimer, the term of this patent is extended or adjusted under 35 U.S.C. 154(b) by 0 days.

(21) Appl. No.: 09/906,463

(22) Filed: Jul. 16, 2001

(65) Prior Publication Data

US 2001/0049498 A1 Dec. 6, 2001

Related U.S. Application Data

(63) Continuation-in-part of application No. 09/772,605, filed on Jan. 30, 2001, which is a continuation-in-part of application No. 09/137,335, filed on Aug. 20, 1998, now Pat. No. 6,187,000.

(51) Int. Cl.[7] .............................................. A61B 17/00
(52) U.S. Cl. ..................................................... 606/190
(58) Field of Search .................. 606/52, 174, 205–210, 606/190

(56) References Cited

U.S. PATENT DOCUMENTS 1,170,324 A * 2/1916 Pomerene ................... 606/198
3,503,398 A * 3/1970 Fogarty et al. ............. 606/207
5,196,023 A * 3/1993 Martin ........................ 606/148
5,354,302 A * 10/1994 Ko ............................. 606/104
5,370,659 A * 12/1994 Sakashita .................... 600/564
5,417,203 A * 5/1995 Tovey et al. ................ 600/106
5,443,479 A * 8/1995 Bressi, Jr. ................... 606/205
5,490,819 A * 2/1996 Nicholas et al. ............ 600/201
5,529,571 A * 6/1996 Daniel ......................... 403/90
5,690,606 A * 11/1997 Slotman ...................... 600/201
5,851,214 A * 12/1998 Larsen et al. ............... 606/170
5,976,161 A * 11/1999 Kirsch et al. ............... 606/149
6,126,671 A * 10/2000 Richards et al. ............ 2/161.7
6,187,000 B1   2/2001 Davison et al.
6,371,968 B1   4/2002 Kogasaka et al.

* cited by examiner

Primary Examiner—Michael J. Milano
Assistant Examiner—Victor Nguyen
(74) Attorney, Agent, or Firm—Tarolli, Sundheim, Covell & Tummino L.L.P.

(57) ABSTRACT

A surgical tool (112, 410) for use in expanding a cannula (10, 150, 250) includes a first leg (114, 414) having a first end (118, 418) engageable with an inner surface (70, 212, 322) of the cannula. A second leg (114, 414) is connected with the first leg (114, 414). The second leg (114, 414) has a second end (118, 418) engageable with the inner surface (70, 212, 322) of the cannula (10, 150, 250). The first and second ends (118, 418) are movable away from each other to apply a radially outwardly directed force to the inner surface (70, 212, 322) of the cannula (10, 150, 250) and cause expansion of the cannula.

20 Claims, 5 Drawing Sheets

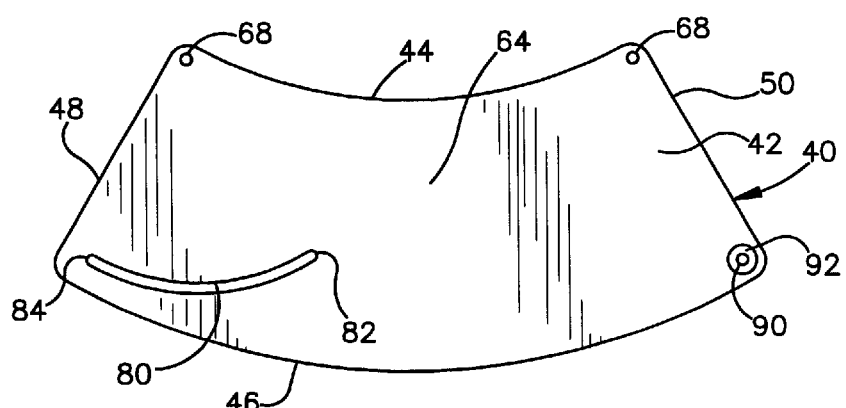
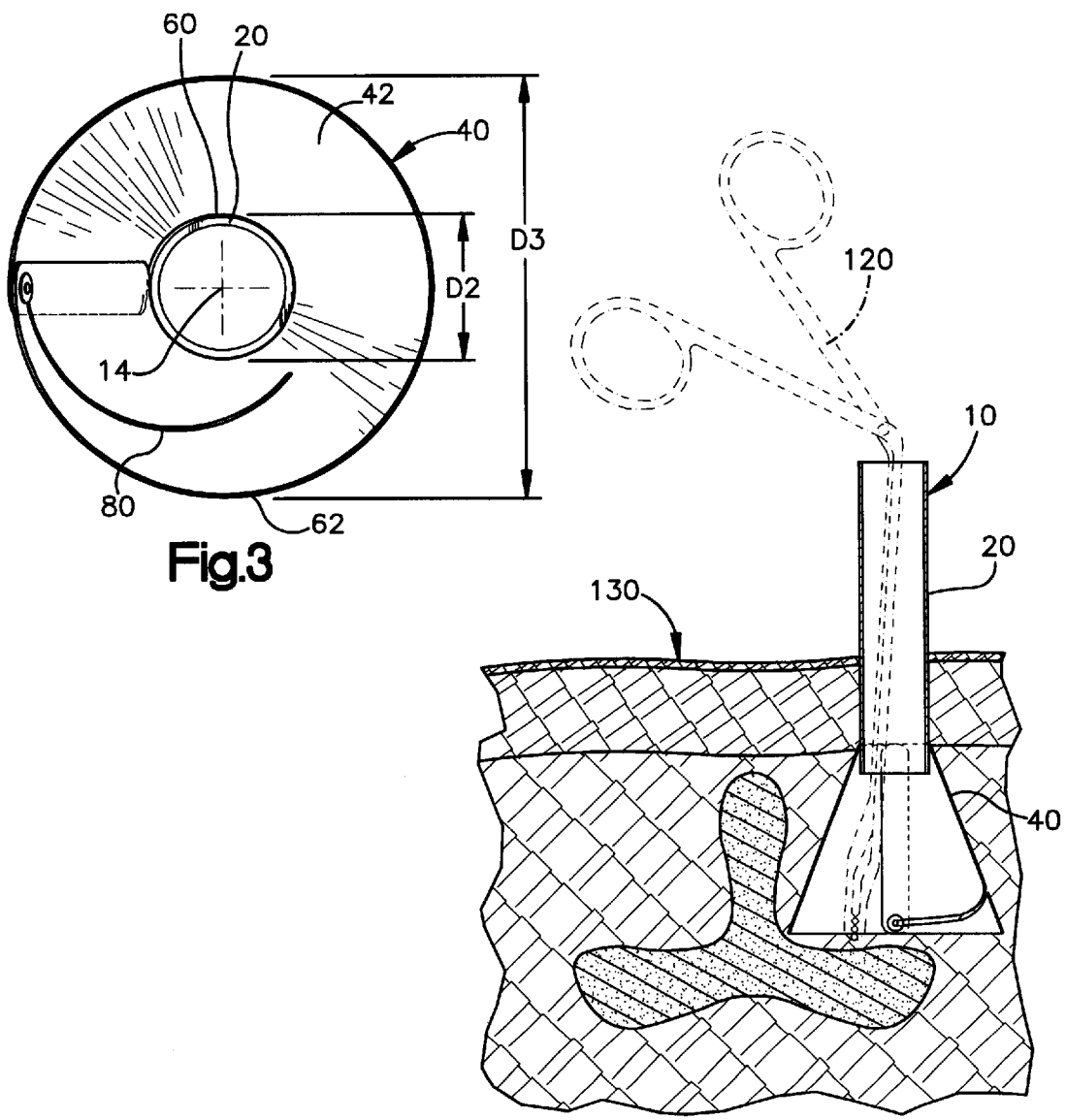

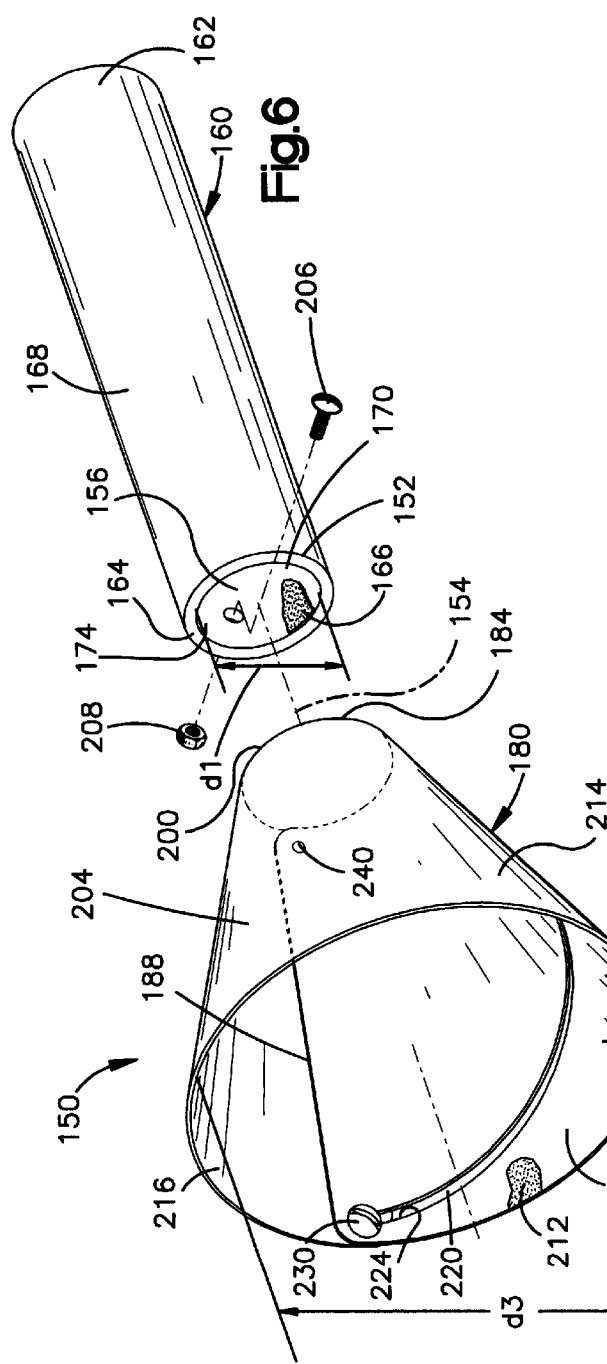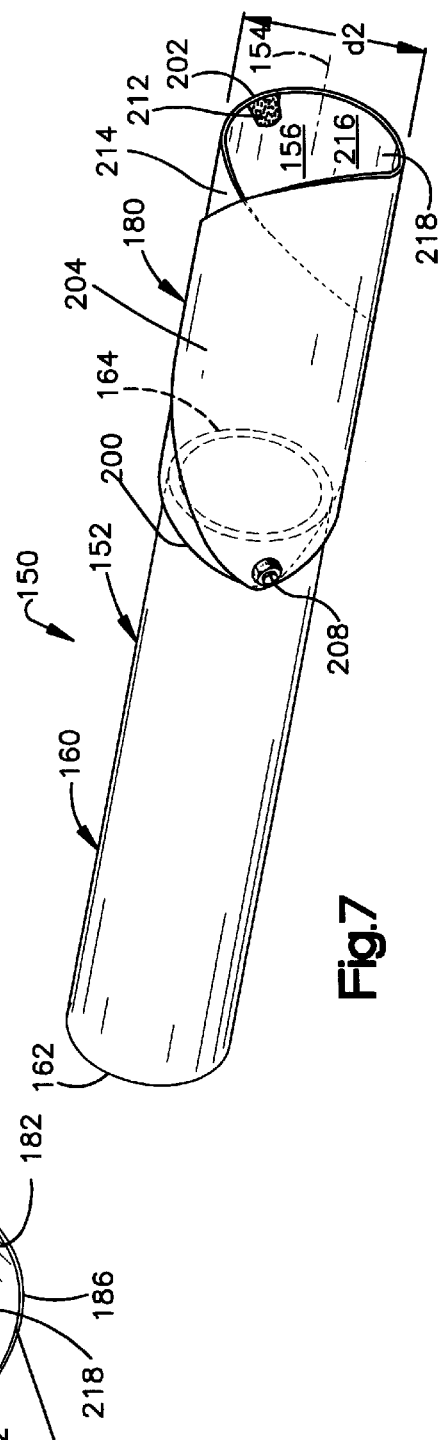

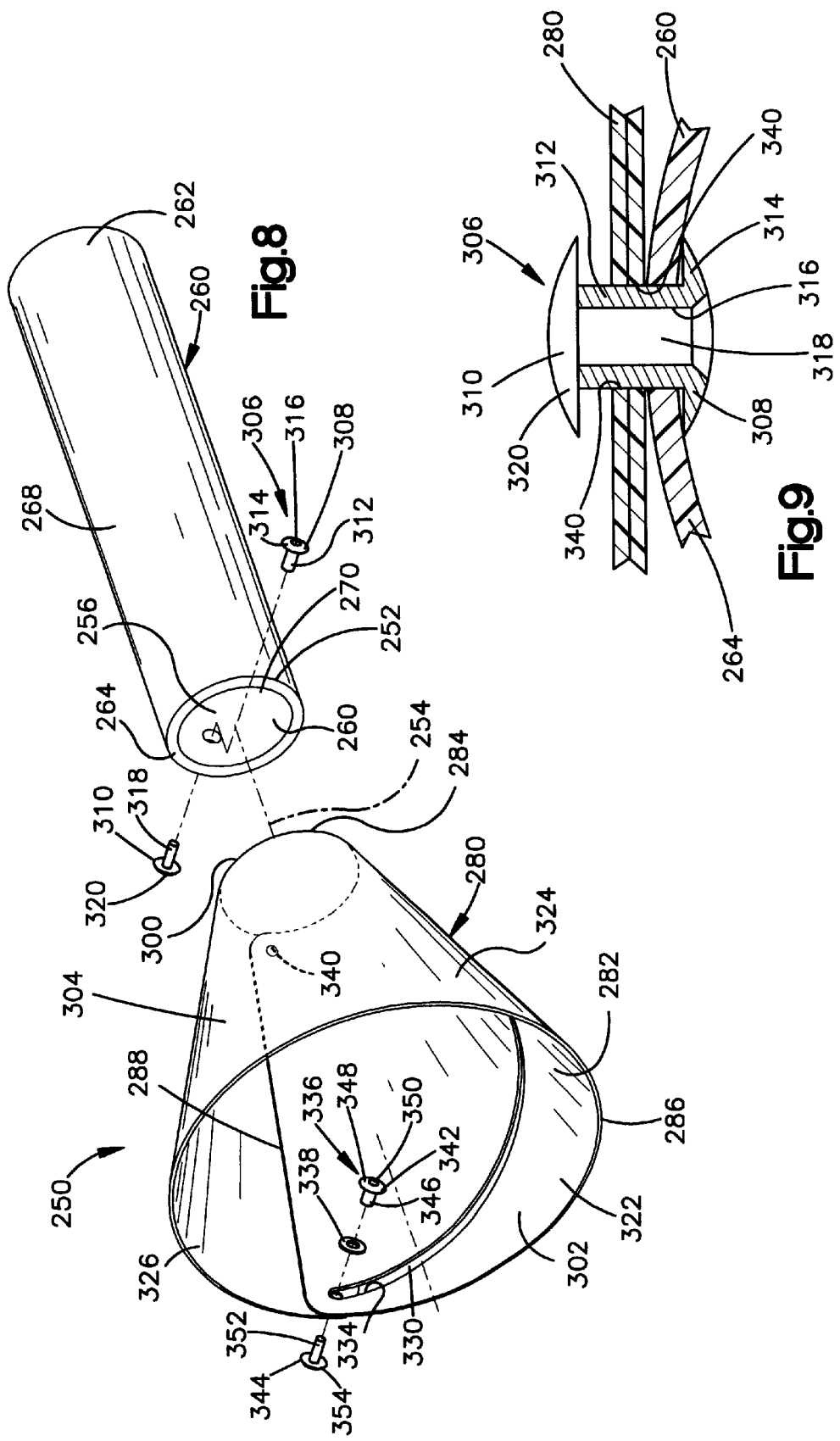

SURGICAL TOOL FOR USE IN EXPANDING A CANNULA

CROSS-REFERENCE TO RELATED APPLICATION

This application is a continuation-in-part of U.S. patent application Ser. No. 09/772,605, filed on Jan. 30, 2001 which is a continuation-in-part of U.S. patent application Ser. No. 09/137,335, filed Aug. 20, 1998, now U.S. Pat. No. 6,187,000, issued Feb. 13, 2001.

FIELD OF THE INVENTION

The present invention relates to a cannula for receiving surgical instruments for performing a surgical procedure on a body, and more specifically, to a surgical tool for use in expanding the cannula.

BACKGROUND OF THE INVENTION

Endoscopic surgical techniques allow a surgical procedure to be performed on a patient's body through a relatively small incision in the body and with a limited amount of body tissue disruption. Endoscopic surgery typically utilizes a tubular structure known as a cannula which is inserted into a small incision in the body. The cannula holds the incision open and serves as a conduit extending between the exterior of the body and the local area inside the body where the surgery is to be performed.

Due to the relatively small size of the passage into the body which is defined by the cannula, certain surgical procedures, such as posterior disectomies and procedures using steerable surgical instruments, have been difficult to perform using endoscopic techniques.

SUMMARY OF THE INVENTION

The present invention is a surgical tool for use in expanding a cannula. The cannula has an inner surface defining a passage through the cannula for receiving surgical instruments. The surgical tool includes a first leg having a first end engageable with the inner surface of the cannula. A second leg is connected with the first leg. The second leg has a second end engageable with the inner surface of the cannula. The first and second ends are movable away from each other to apply a radially outwardly directed force to the inner surface of the cannula and cause expansion of the cannula.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 3 is a schematic end view showing the cannula of FIG. 1 in the expanded condition;

FIG. 4 is a rollout view of a part of the cannula of FIG. 1;

FIG. 5 is a schematic sectional view of the cannula of FIG. 1 during a surgical procedure;

FIG. 6 is a perspective view of a part of another embodiment of a surgical cannula, the cannula being shown in an expanded condition;

FIG. 7 is a perspective view of the part of the cannula of FIG. 6, the cannula being shown in a contracted condition;

FIG. 8 is a perspective view of a part of another embodiment of a surgical cannula, the cannula being shown in an expanded condition;

FIG. 9 is a sectional view of a portion of the cannula of FIG. 8 showing a rivet connecting a first tubular portion to a second tubular portion.

DESCRIPTION OF THE INVENTION

The present invention is directed to a surgical tool for use in expanding a cannula for performing a surgical procedure on the body of a patient. The present invention is applicable to a variety of surgical procedures in which endoscopic surgical techniques are used.

Figure 1:
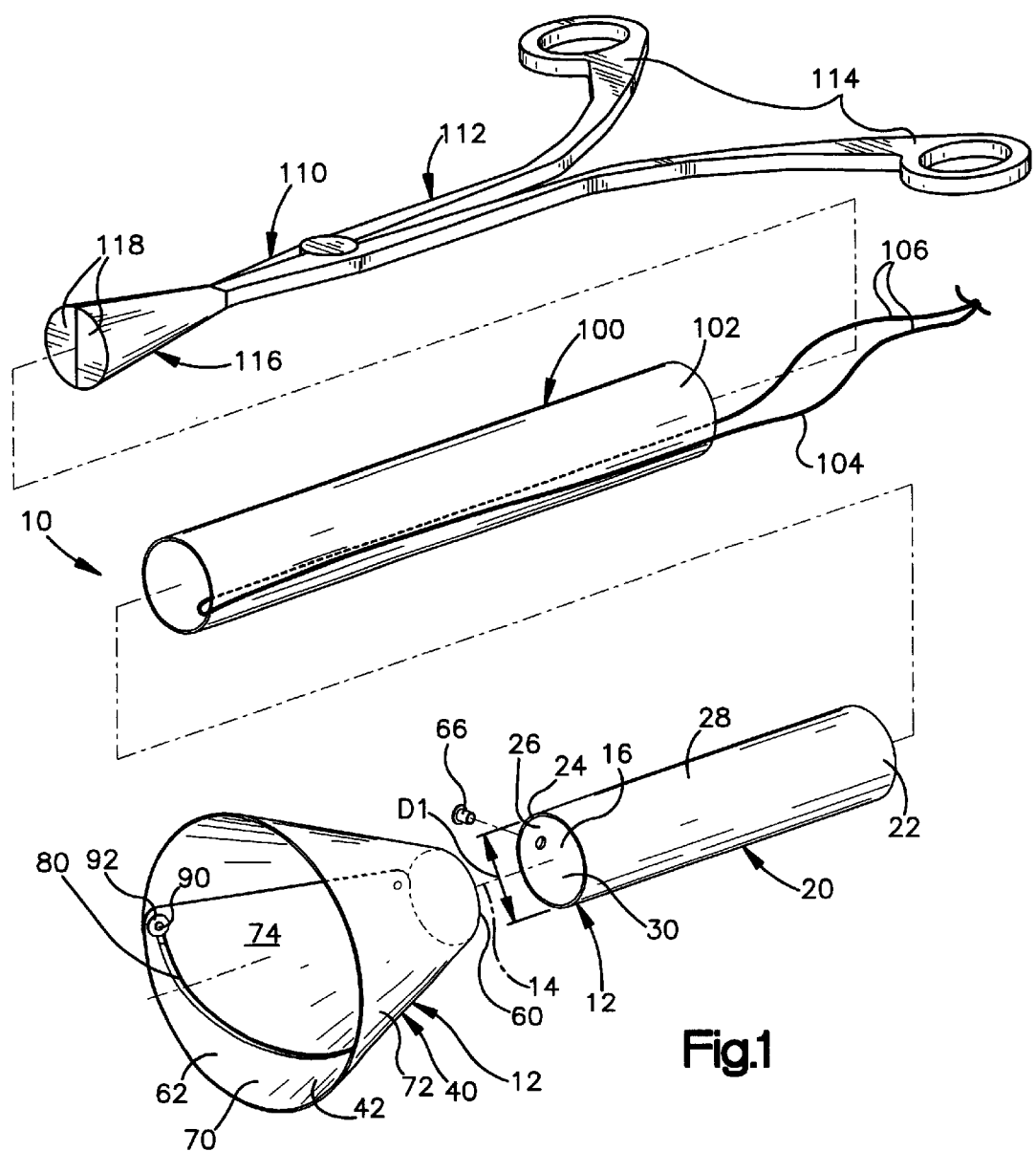
FIG. 1 is an exploded perspective view of a surgical cannula with a surgical tool constructed in accordance with a first embodiment of the present invention, the cannula being shown in an expanded condition.

FIG. 1 illustrates a cannula 10. The cannula 10 is a tubular structure 12 centered on an axis 14. The tubular structure 12 defines a passage 16 through the cannula 10. Surgical instruments are inserted into the body during endoscopic surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material such as a radiolucent material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 which is preferably in the range from 10 mm to 25 mm or approximately 0.4 inches to approximately 1.0 inches.

The second tubular portion 40 of the tubular structure 12 is attached to the distal end 24 of the first tubular portion 20. The second tubular portion is preferably made from stainless steel, but could alternatively be made from another suitable material such as a radiolucent material.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single suitable fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 10 which extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A suitable guide member, such as guide pin 90, is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured to an inner end of the guide pin 90 to retain the guide pin in the arcuate slot 80.

Figure 2:
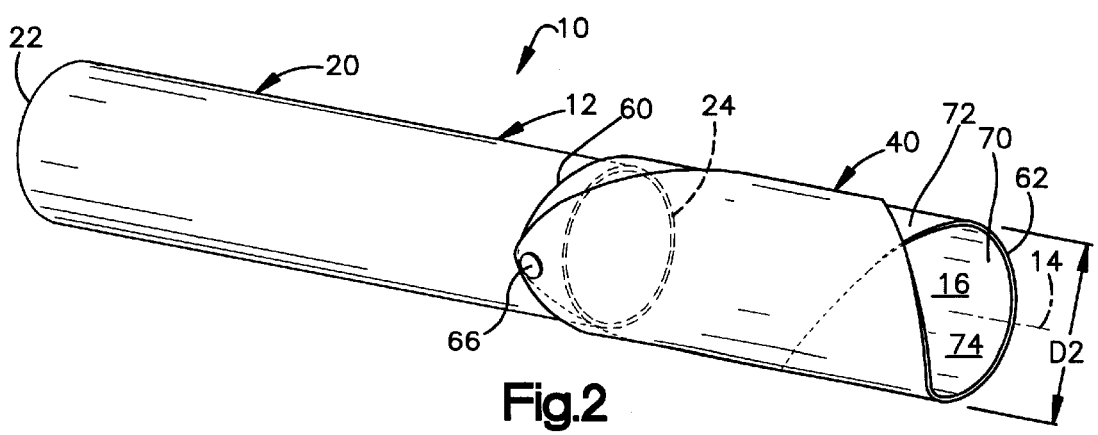
FIG. 2 is a perspective view of the cannula of FIG. 1 with parts removed for clarity, the cannula being shown in a contracted condition.

The second tubular portion 40 of the tubular structure 12 is expandable from a contracted condition shown in FIG. 2 to an expanded condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) which is approximately equal to the diameter D1 of the first tubular portion 20. Thus, the cross-sectional area of the second passage portion 74 at the second end 62 of the second tubular portion 40, which is a function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a conical configuration. At the second end 62 of the second tubular portion 40, the second passage portion 74 has a diameter D3 (FIG. 3) which is larger than the diameter D2 of the second passage portion at the first end 60. Preferably, the diameter D3 of the second passage portion 74 at the second end 62 of the second tubular portion is 40% to 90% greater than the diameter D2 of the second passage portion at the first end 60. Thus, in the expanded condition, the cross-sectional area of the second passage portion 74 at the second end 62 of the second tubular portion 40, which is a function of the diameter D3, is greater than the cross-sectional area of the second passage portion at the first end 60 of the second tubular portion. Although the cross-sectional area at the second end 62 is shown as being circular in FIG. 3, it is contemplated that the cross-sectional area at the second end 62 could be any shape, such as oval shaped.

The cannula 10 includes an outer layer 100 (FIG. 1) for maintaining the second tubular portion 40 of the cannula in the contracted condition. It is contemplated that other suitable means for maintaining the second tubular portion 40 in the contracted condition could be employed. In accordance with a preferred embodiment of the present invention, the outer layer 100 comprises a section of plastic tubing 102 which is heat shrunk over both the first and second tubular portions 20 and 40 to hold the second tubular portion in the contracted condition.

In addition, a loop of polyester string 104 for tearing the heat shrink tubing 102 is wrapped around the heat shrink tubing so that it extends both underneath and on top of the tubing. An outer end 106 of the string 104 extends beyond the tubing 102.

The cannula 10 further includes an actuatable device 110 for expanding the second tubular portion 40 from the contracted condition to the expanded condition. In accordance with a first embodiment of the present invention, the actuatable device 110 comprises a manually operated expansion tool 112. The expansion tool 112 resembles a common pair of scissors and has a pair of legs 114 pivotally connected to one another. The expansion tool 112 includes a frustoconical end section 116 formed by a pair of frustoconical halves 118. Each of the frustoconical halves 118 extends from a respective one of the legs 114 of the expansion tool 112. It is contemplated that other suitable means for expanding the second tubular portion 40 toward the expanded condition could be employed, such as an inflatable balloon (not shown).

During an endoscopic surgical procedure, the cannula 10 is inserted through an incision into the body of a patient in the contracted condition. The cannula 10 is inserted through the incision using step dilation. The second tubular portion 40 is inserted inside the body. The first tubular portion 20 is inserted into the incision so that the first tubular portion extends from an exterior of the body to inside the body.

The outer end 106 of the string 104 is then manually pulled on by the surgeon. Pulling on the string 104 tears the heat shrink tubing 102. With the heat shrink tubing 102 torn, the second tubular portion 40 of the cannula 10 is thereby released for expansion toward the expanded condition.

Next, the expansion tool 112 is inserted into the passage 16 in the cannula 10 until the frustoconical end section 114 is located at the second end 62 of the second tubular portion 40. The legs 114 of the expansion tool 112 are manually separated, causing the frustoconical halves 118 to separate also. As the halves 118 separate, a radially outwardly directed force is exerted on the inner surface 70 of the second tubular portion 40 by the halves 118, causing the second tubular portion to expand toward the expanded condition.

Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 120 in FIG. 5) can be received through the cannula 10 and inserted into a patient's body 130.

The expandable second tubular portion 40 of the cannula 10 provides a significantly larger working area for the surgeon inside the body 130 within the confines of the cannula. As a result, the simultaneous use of a number of endoscopic surgical instruments, including but not limited to steerable instruments, shavers, dissectors, scissors, forceps, retractors, dilators, and endoscopes, is made possible by the expandable cannula 10.

Figure 10:
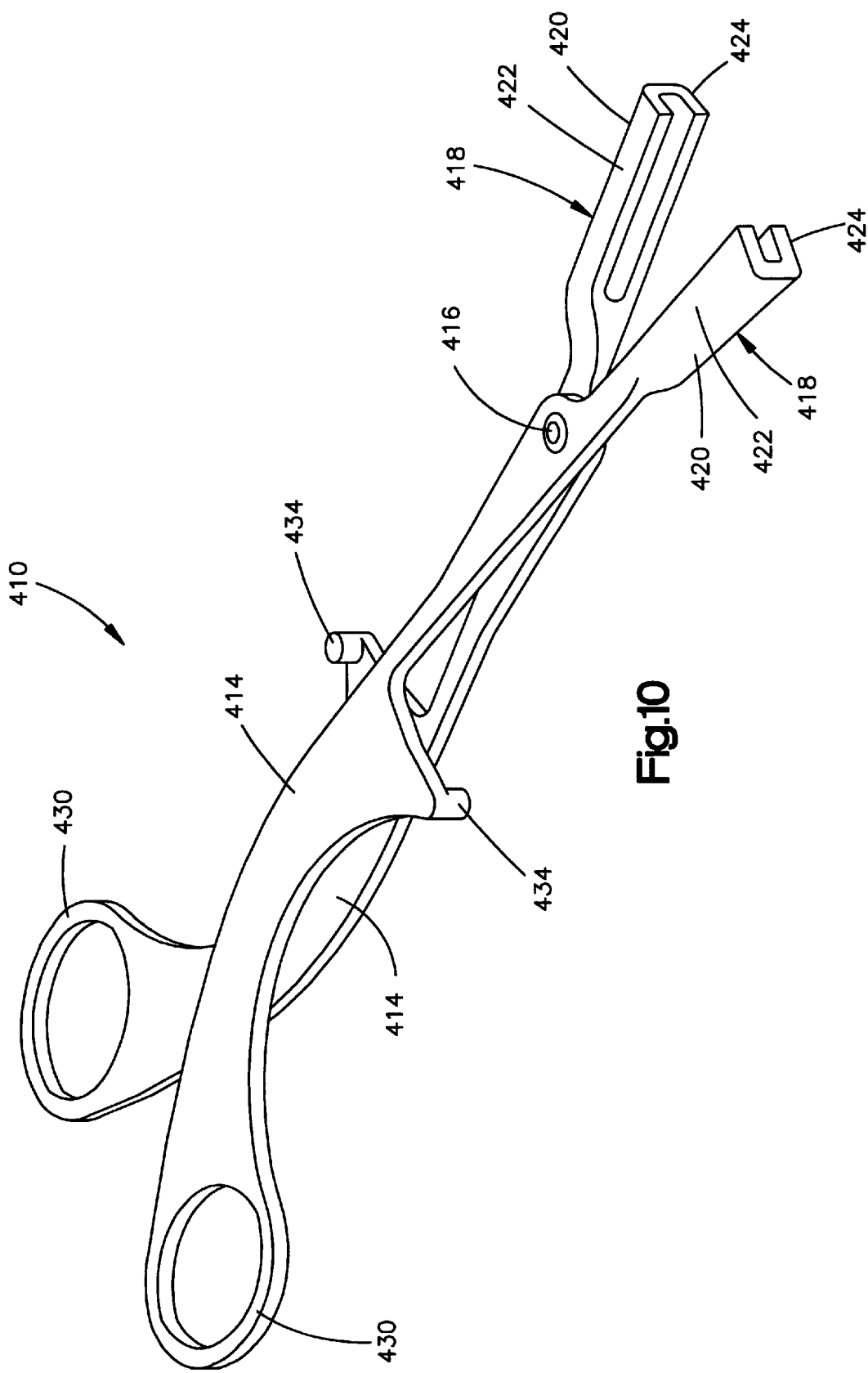
FIG. 10 is a perspective view of a surgical tool constructed in accordance with a second embodiment of the present invention.

A surgical tool 410 constructed according to a second embodiment of the present invention is illustrated in FIG. 10. The surgical tool 410 resembles a common pair of scissors and has a pair of legs 414 pivotally connected to each other by a pivot connection 416. Each of the legs 414 has an end 418 with a tapered outer surface 420. Each of the ends 418 has a generally U-shaped cross-section with outer surfaces 422 and 424. The surfaces 422 and 424 extend generally parallel to each other and transverse to the tapered surface 420.

The legs 414 have handles 430 opposite the ends 418. The handles 430 may be grasped by a surgeon to move the ends 418 away from each other. The handles 430 are moved toward each other to move the ends 418 away from each other. Each of the legs 414 has a stop 434 that engages the other leg to limit the movement of the ends 418 away from each other.

The expansion tool 410 is inserted into the passage 16 in the cannula 10 until the ends 418 are located at the second end 62 of the second tubular portion 40. The legs 418 of the expansion tool 410 are manually separated by moving the handles 430 toward each other. As the handles 430 are moved toward each other, the ends 418 separate. As the ends 418 separate, a radially outwardly directed force is exerted on the inner surface 70 of the second tubular portion 40 by the ends 418, causing the second tubular portion to expand toward the expanded condition. Under the force of the expanding expansion tool 410, the guide pin 90 slides from the first terminal end 82 of the arcuate slot 80 toward the second terminal end 84 of the arcuate slot to permit the expansion of the second tubular portion 40. The expansion tool 410 can be rotated about the axis 14 to ensure that the second tubular portion 40 of the cannula 10 is completely expanded to the expanded condition. The expansion tool 410 is then collapsed and removed so that one or more surgical instruments can be received through the cannula 10 and inserted into a patient's body.

A cannula 150 constructed according to another embodiment is illustrated in FIGS. 6–7. The cannula 150 includes a tubular structure 152 centered on an axis 154. The tubular structure 152 defines a passage 156 through the cannula 150. Surgical instruments are inserted into the body during endoscopic surgery through the passage 156.

The tubular structure 152 (FIG. 6) comprises a first tubular portion 160 and a second tubular portion 180 attached to the first tubular portion. The first tubular portion 160 is preferably made of a length of stainless steel tubing, but could alternatively be made of another suitable material, such as a radiolucent material. The first tubular portion 160 has a proximal end 162 and a distal end 164. Parallel cylindrical inner and outer surfaces 166 and 168 extend between the ends 162, 164 of the first tubular portion 160. The first tubular portion 160 has a thickness measured perpendicular to the surfaces 166 and 168 in the range of 0.02 inches to 0.04 inches or approximately 0.5 mm to approximately 1.0 mm.

The inner surface 166 defines a first passage portion 170 of the passage 156 through the cannula 150. The first passage portion 170 has a diameter d1 which is preferably in the range from 10 mm to 25 mm or approximately 0.4 inches to approximately 1.0 inches. The inner surface 166 has a non-reflective coating 174. The non-reflective coating 174 reduces glare on any video image produced by an endoscope inserted through the passage 156. It is contemplated that the inner surface 166 may not have the coating 174.

The second tubular portion 180 (FIG. 6) of the tubular structure 152 is attached to the distal end 164 of the first tubular portion 160. The second tubular portion 180 is preferably made from stainless steel, but could alternatively be made from another suitable material, such as a radiolucent material.

The second tubular portion 180 includes an arcuate segment 182 of sheet stock. The arcuate segment 182 includes first and second arcuate edges 184 and 186. The arcuate segment 182 also includes a first planar edge 188 and a second planar edge extending between the arcuate edges 184 and 186, which is not shown in FIG. 6. The first and second planar edges are rolled in an overlapping manner to form the tubular configuration of the second tubular portion 180.

When the second tubular portion 180 has been rolled into its tubular configuration, the first and second arcuate edges 184 and 186 define oppositely disposed first and second ends 200 and 202 of the second tubular portion. The first and second ends 200 and 202 are connected by a central portion 204. The first end 200 of the second tubular portion 180 is attached to the distal end 164 of the first tubular portion 160 by a suitable fastener, such as a screw 206 and nut 208 threaded on the screw. It is contemplated that the second tubular portion 180 could be connected to the first tubular portion 160 by a rivet. The screw 206 extends through two aligned apertures 240 at the first end 200 of the second tubular portion 180. The first end 200 of the second tubular portion 180 is pivotable about the screw 206.

The second tubular portion 180 includes parallel inner and outer surfaces 212 and 214 extending between the first and second ends 200 and 202. The inner surface 212 defines a second passage portion 216 of the passage 156 through the cannula 150 which extends as a continuation of the first passage portion 170 in the first tubular portion 160. The second tubular portion 180 has a thickness measured perpendicular to the surfaces 212 and 214 in the range of 0.003 inches to 0.006 inches or approximately 0.075 mm to approximately 0.15 mm. The inner surface 212 has a non-reflective coating 218. The non-reflective coating 218 reduces glare on any video image produced by an endoscope inserted through the passage 156. It is contemplated that the inner surface 212 may not have the coating 218.

An arcuate slot 220 (FIG. 6) is formed in the second tubular portion 180 and extends between the inner and outer surfaces 212 and 214 of the second tubular portion. The arcuate slot 220 extends along a curvilinear path in the central portion 204 of the second tubular portion 180 toward the end 184 of the second tubular portion. The arcuate slot 220 has a first terminal end (not shown) located in the central portion 204 of the second tubular portion 180. A second terminal end 224 of the arcuate slot 220 is located adjacent the intersection of the second arcuate edge 186 and the planar edge 188 of the arcuate segment 182.

A guide member or screw 230 is attached to the inner surface 212 of the second tubular portion 180 adjacent the intersection of the second arcuate edge 186 and the planar edge (not shown). It is contemplated that a guide pin could be used instead of the screw 230. In the tubular configuration of the second tubular portion 180, the guide member 230 is located in the arcuate slot 220 and is movable along the curvilinear path of the arcuate slot.

The second tubular portion 180 of the tubular structure 152 is expandable from a contracted condition, shown in FIG. 7, to an expanded condition, shown in FIG. 6. In the contracted condition (FIG. 7), the guide member 230 is located in the first terminal end (not shown) of the arcuate slot 220 in the second tubular portion 180 and the second passage portion 216 defined by the second tubular portion is cylindrical in shape. The second passage 216 has a generally constant diameter d2 which is approximately equal to the diameter d1 of the first tubular portion 160. Thus, the cross-sectional area of the second passage portion 216 at the second end 202 of the second tubular portion 180, which is a function of the diameter d2, is approximately the same as the cross-sectional area at the first end 200 of the second tubular portion and is approximately the same as the cross-sectional area of the first passage portion 170 in the first tubular portion 160.

In the expanded condition (FIG. 6), the guide member 230 is located in the second terminal end 224 of the arcuate slot 220 in the second tubular portion 180 and the second tubular portion has a conical configuration. At the second end 202 of the second tubular portion 180, the second passage portion 216 has a diameter d3 which is larger than the diameter d2 of the second passage portion at the first end 200. Preferably, the diameter d3 of the second passage portion 216 at the second end 202 of the second tubular portion is 40% to 90% greater than the diameter d2 of the second passage portion at the first end 200. Thus, in the expanded condition, the cross-sectional area of the second passage portion 216 at the second end 202 of the second tubular portion 180, which is function of the diameter d3, is greater than the cross-sectional area of the second passage portion at the first end 200 of the second tubular portion. Although the cross-sectional area at the second end 202 is shown as being circular in FIG. 6, it is contemplated that the cross-sectional area at the second end 202 could be any shape, such as oval shaped.

The cannula 150 includes an outer member (not shown) for maintaining the second tubular portion 180 of the cannula in the contracted condition. It is contemplated that other suitable means for maintaining the second tubular portion 180 in the contracted condition could be employed. In accordance with the present invention, the outer member may be similar to the layer 100 shown in FIG. 1 and include a section of plastic tubing which is heat shrunk over both the first and second tubular portions 160 and 180 to hold the second tubular portion in the contracted condition. In addition, a loop of polyester string (not shown) for tearing the heat shrink tubing is wrapped around the heat shrink tubing so that it extends both underneath and on top of the tubing. An outer end of the string extends beyond the tubing.

During an endoscopic surgical procedure, the cannula 150 is inserted through an incision into the body of a patient in the contracted condition. The cannula 150 is inserted through the incision using step dilation. The second tubular portion 180 is inserted inside the body. The first tubular portion 160 is inserted into the incision so that the first tubular portion extends from an exterior of the body to inside the body.

The outer end of the string is then manually pulled on by the surgeon. Pulling on the string tears the heat shrink tubing. With the heat shrink tubing torn, the second tubular portion 180 of the cannula 150 is thereby released for expansion toward the expanded condition.

Next, one of the expansion tools 112 and 410, shown in FIGS. 1 and 10, is inserted into the passage 156 in the cannula 150 until the frustoconical end section 118 or 418 is located at the second end 202 of the second tubular portion 180. The legs 114 or 414 of the expansion tool 112 or 410 are manually separated, causing the frustoconical halves 118 or ends 418 to separate also. As the halves 118 or ends 418 separate, a radially outwardly directed force is exerted on the inner surface 212 of the second tubular portion 180 by the halves 118 or ends 418, causing the second tubular portion to expand toward the expanded condition. Under the force of the expanding expansion tool 112 or 410, the guide member 230 slides from the first terminal end of the arcuate slot 220 to the second terminal end of the arcuate slot to permit the expansion of the second tubular portion 180. The expansion tool 112 or 410 can be rotated about the axis 154 to ensure that the second tubular portion 180 of the cannula 150 is completely expanded to the expanded condition. The expansion tool 112 or 410 is then collapsed and removed so that one or more surgical instruments can be received through the cannula 150 and inserted into a patient's body.

The expandable second tubular portion 180 of the cannula 150 provides a significantly larger working area for the surgeon inside the body within the confines of the cannula. As a result, the simultaneous use of a number of endoscopic surgical instruments, including but not limited to steerable instruments, shavers, dissectors, scissors, forceps, retractors, dilators, and endoscopes, is made possible by the expandable cannula 150.

A cannula 250 constructed according to another embodiment is illustrated in FIGS. 8–9. In the embodiment of the cannula 150 illustrated in FIGS. 6–7 the tubular portions 160 and 180 are connected by a screw 206 and nut 208 and the guide member is a screw 230. In the embodiment of the cannula 250 illustrated in FIGS. 8–9 the tubular portions are connected by a rivet and the guide member is a rivet. The cannula 250 is generally similar to the cannula 150 shown in FIGS. 6–7. Accordingly, only the rivets will be described in detail.

The cannula 250 (FIG. 8) includes a tubular structure 252 centered on an axis 254. The tubular structure 252 defines a passage 256 through the cannula 250. The tubular structure 252 includes a first tubular portion 260 and a second tubular portion 280 attached to the first tubular portion. The first tubular portion 260 has a proximal end 262 and a distal end 264. Parallel cylindrical inner and outer surfaces 266 and 268 extend between the ends 262, 264 of the first tubular portion 260. The inner surface 266 defines a first passage portion 270 of the passage 256 through the cannula 250. The inner surface 266 could have a non-reflective coating (not shown).

The second tubular portion 280 (FIG. 8) of the tubular structure 252 is attached to the distal end 264 of the first tubular portion 260. The second tubular portion 280 includes an arcuate segment 282 of sheet stock. The arcuate segment 282 includes first and second arcuate edges 284 and 286. The arcuate segment 282 also includes a first planar edge 288 and a second planar edge extending between the arcuate edges 284 and 286, which is not shown in FIG. 8. The first and second planar edges are rolled in an overlapping manner to form the tubular configuration of the second tubular portion 280.

When the second tubular portion 280 has been rolled into its tubular configuration, the first and second arcuate edges 284 and 286 define oppositely disposed first and second ends 300 and 302 of the second tubular portion. The first and second ends 300 and 302 are connected by a central portion 304. The first end 300 of the second tubular portion 280 is attached to the distal end 264 of the first tubular portion 260 by a rivet 306. The rivet 306 extends through two aligned apertures 340 at the first end 300 of the second tubular portion 280. The first end 300 of the second tubular portion 280 is pivotable about the rivet 306.

The rivet 306 (FIGS. 8 and 9) has a first portion 308 and a second portion 310. The first portion 308 has a shaft 312 extending from a head 314. The shaft 312 extends through the apertures 340 in the tubular portion 280 and the head engages the inner surface 266 of the first tubular portion 260. A cylindrical opening 316 extends through the shaft 312 and the head 314.

The second portion 310 of the rivet 306 has a shaft 318 extending from a head 320. The shaft 318 extends into the opening 316 in the first portion 308 of the rivet 306 and the head 320 engages the second tubular portion 280. The shaft 318 of the second portion 310 extends into the opening 316 in the first portion 308 to connect the first and second portions of the rivet 306 and pivotally connect the second tubular portion 280 to the first tubular portion 260.

The second tubular portion 280 (FIG. 8) includes parallel inner and outer surfaces 322 and 324 extending between the first and second ends 300 and 302. The inner surface 322 defines a second passage portion 326 of the passage 256 through the cannula 250 which extends as a continuation of the first passage portion 270 in the first tubular portion 260. The inner surface 322 could have a non-reflective coating (not shown).

An arcuate slot 330 is formed in the second tubular portion 280 and extends between the inner and outer surfaces 322 and 324 of the second tubular portion. The arcuate slot 330 extends along a curvilinear path in the central portion 304 of the second tubular portion 280 toward the end 284 of the second tubular portion. The arcuate slot 330 has a first terminal end (not shown) located in the central portion 304 of the second tubular portion 280. A second terminal end 334 of the arcuate slot 330 is located adjacent the intersection of the second arcuate edge 286 and the planar edge 288 of the arcuate segment 282.

A rivet 336 is attached to the inner surface 322 of the second tubular portion 280 adjacent the intersection of the second arcuate edge 286 and the planar edge (not shown). It is contemplated that a guide pin could be used instead of the rivet 336. In the tubular configuration of the second tubular portion 280, the rivet 336 is located in the arcuate slot 330 and is movable along the curvilinear path of the arcuate slot. The rivet 336 extends through a washer 338 to retain the rivet in the arcuate slot 330.

The rivet 336 is generally similar to the rivet 306 and, therefore, will not be described in detail. The rivet 336 has a first portion 342 and a second portion 344. The first portion 342 has a shaft 346 extending from a head 348. The shaft 346 extends through the slot 330 and the head 348 engages the washer 338. A cylindrical opening 350 extends through the shaft 346 and the head 348.

The second portion 344 of the rivet 336 has a shaft 352 extending from a head 354. The shaft 352 extends into the opening 350 in the first portion 342 of the rivet 336 and the head 354 engages the outer surface 324 of the second tubular portion 280. The shaft 352 extends into the opening 350 to connect the first portion 342 of the rivet 336 to the second portion 344.

The second tubular portion 280 of the tubular structure 252 is expandable from a contracted condition to an expanded condition, shown in FIG. 8. In the contracted condition the rivet 336 is located in the first terminal end (not shown) of the arcuate slot 330 in the second tubular portion 280 and the second passage portion 326 defined by the second tubular portion is cylindrical in shape. The second passage portion 326 has a generally constant diameter which is approximately equal to the diameter of the first tubular portion 260. Thus, the cross-sectional area of the second passage portion 326 at the second end 302 of the second tubular portion 280 is approximately the same as the cross-sectional area at the first end 300 of the second tubular portion and is approximately the same as the cross-sectional area of the first passage portion 270 in the first tubular portion 260.

In the expanded condition (FIG. 8), the rivet 336 is located in the second terminal end 334 of the arcuate slot 330 in the second tubular portion 280 and the second tubular portion has a conical configuration. At the second end 302 of the second tubular portion 280, the second passage portion 326 has a diameter which is larger than the diameter of the second passage portion at the first end 300. Thus, in the expanded condition, the cross-sectional area of the second passage portion 326 at the second end 302 of the second tubular portion 280 is greater than the cross-sectional area of the second passage portion at the first end 300 of the second tubular portion. Although the cross-sectional area at the second end 302 is shown as being circular in FIG. 8, it is contemplated that the cross-sectional area at the second end 302 could be any shape, such as oval shaped.

During an endoscopic surgical procedure, the cannula 250 is inserted through an incision into the body of a patient in the contracted condition. The cannula 250 is inserted through the incision using step dilation. The second tubular portion 280 is inserted inside the body. The first tubular portion 260 is inserted into the incision so that the first tubular portion extends from an exterior of the body to inside the body.

Heat shrink tubing is torn from the cannula 250 by the surgeon. With the heat shrink tubing torn, the second tubular portion 280 of the cannula 250 is thereby released for expansion toward the expanded condition. Next, one of the expansion tools 112, 410 shown in FIGS. 1 and 10, is inserted into the passage 256 in the cannula 250 until the frustoconical end section 118 or 418 is located at the second end 302 of the second tubular portion 280. The legs 114 or 414 of the expansion tool 112 or 410 are manually separated, causing the frustoconical halves 118 or ends 418 to separate also. As the halves 118 or ends 418 separate, a radially outwardly directed force is exerted on the inner surface 312 of the second tubular portion 280 by the halves 118 or ends 418, causing the second tubular portion to expand toward the expanded condition. Under the force of the expanding expansion tool 112 or 410, the rivet 336 slides from the first terminal end of the arcuate slot 330 to the second terminal end 334 of the arcuate slot to permit the expansion of the second tubular portion 280. The expansion tool 112 or 410 is then collapsed and removed so that one or more surgical instruments can be received through the cannula 250 and inserted into a patient's body.

The expandable second tubular portion 280 of the cannula 250 provides a significantly larger working area for the surgeon inside the body within the confines of the cannula. As a result, the simultaneous use of a number of endoscopic surgical instruments, including but not limited to steerable instruments, shavers, dissectors, scissors, forceps, retractors, dilators, and endoscopes, is made possible by the expandable cannula 250.

It is contemplated that the cannula 10, 150, and/or the cannula 250 described herein could be the centerpiece of an endoscopic surgical kit with the surgical tool 112 and/or 410 which would include an assortment of surgical instruments designed and/or selected for use with the cannula.

From the above description of the invention, those skilled in the art will perceive improvements, changes and modifications. Such improvements, changes and modifications within the skill of the art are intended to be covered by the appended claims.

Having described the invention, the following is claimed:

1. A surgical tool for use in expanding a cannula, the cannula having an inner surface defining a passage through the cannula for receiving surgical instruments, said surgical tool comprising:

a first leg having a first end engageable with the inner surface of the cannula; and a second leg connected with said first leg, said second leg having a second end engageable with the inner surface of the cannula, said first and second ends being moveable away from each other to apply a radially outwardly directed force to the inner surface of the cannula and cause expansion of the cannula.

2. A surgical tool as set forth in claim 1 wherein said second leg is pivotally connected to said first leg.

3. A surgical tool as set forth in claim 2 wherein said first leg has a first handle opposite said first end and said second leg has a second handle opposite said second end, said first and second handles being movable toward each other to pivot said first and second legs relative to each other and move said first and second ends away from each other.

4. A surgical tool as set forth in claim 1 wherein each of said first and second ends has a tapered outer surface engageable with the inner surface of the cannula.

5. A surgical tool as set forth in claim 4 wherein said first and second ends of said first and second legs define a frustoconical end section of said surgical tool.

6. A surgical tool as set forth in claim 5 wherein each of said first and second ends of said first and second legs includes a frustoconical half, said frustoconical halves defining said frustoconical end section.

7. A surgical tool as set forth in claim 1 wherein said first leg has a stop engageable with said second leg to limit movement of said first and second ends away from each other.

8. A surgical tool as set forth in claim 7 wherein said second leg has a stop engageable with said first leg to limit the movement of said first and second ends away from each other.

9. A surgical tool as set forth in claim 1 wherein each of said first and second ends has a generally U-shaped cross-section.

10. A surgical tool as set forth in claim 9 wherein each of said first and second ends has first and second outer surfaces extending generally parallel to each other.

11. A surgical tool for use in expanding a cannula, the cannula having an inner surface defining a passage through the cannula for receiving surgical instruments, said surgical tool comprising:

a first leg having a first end means for engaging the inner surface of the cannula; and a second leg connected with said firs leg, said second leg having a second end means for engaging the inner surface of the cannula, and means for moving said first and second end means away from each other, said first and second end means including means for applying a radially outwardly directed force to the inner surface of the cannula and for causing expansion of the cannula.

12. A surgical tool as set forth in claim 11 wherein said second leg is pivotally connected to said first leg.

13. A surgical tool as set forth in claim 12 wherein said first leg has a first handle opposite said first end means and said second leg has a second handle opposite said second end means, said first and second handles being movable toward each other to pivot said first and second legs relative to each other and move said first and second end means away from each other.

14. A surgical tool as set forth in claim 11 wherein each of said first and second ene means has a tappered outer surface means for engaging the inner surface of the cannula.

15. A surgical tool as set forth in claim 14 wherein said first and second end means of said first and second legs define a frustoconical end section of said surgical tool.

16. A surgical tool as set forth in claim 15 wherein each of said first and second end means of said first and second legs includes a frustoconical half, said frustoconical halves defining said frustoconical end section.

17. A surgical tool as set forth in claim 11 wherein said first leg has a stop means for engaging said second leg to limit movement of said first and second means away from each other.

18. A surgical tool as set forth in claim 17 wherein said second leg has a stop means for engaging said first leg to limit the movement of said first and second end means away from each other.

19. A surgical tool as set forth in claim 11 wherein each of said first and second end means has a generally U-shaped cross-section.

20. A surgical tool as set forth in claim 19 wherein each of said first and second end means has first and second outer surfaces extending generally parallel to each other.

* * * * *